(12) United States Patent
Boehm et al.

(10) Patent No.: US 7,980,247 B2
(45) Date of Patent: Jul. 19, 2011

(54) THERAPEUTIC AEROSOL DEVICE

(75) Inventors: Andreas Boehm, Reichling (DE); Christiane Horn, Munich (DE); Martin Luber, Munich (DE); Markus Mornhinweg, Diessen (DE); Titus Selzer, Munich (DE); Johann Zimmermann, Bergheim (DE)

(73) Assignee: PARI GmbH Spezialisten fuer effektive Inhalation, Starnberg (DE)

( * ) Notice: Subject to any disclaimer, the term of this patent is extended or adjusted under 35 U.S.C. 154(b) by 734 days.

(21) Appl. No.: 10/519,011

(22) PCT Filed: Aug. 27, 2003

(86) PCT No.: PCT/EP03/09862
§ 371 (c)(1),
(2), (4) Date: Aug. 5, 2005

(87) PCT Pub. No.: WO2004/020029
PCT Pub. Date: Mar. 11, 2004

(65) Prior Publication Data
US 2006/0162722 A1    Jul. 27, 2006

(30) Foreign Application Priority Data
Aug. 27, 2002 (DE) .................. 102 39 321

(51) Int. Cl.
*A61M 15/08* (2006.01)
*A61M 15/00* (2006.01)
*A61M 16/00* (2006.01)
*A62B 18/02* (2006.01)

(52) U.S. Cl. ......... 128/207.18; 128/201.18; 128/203.12; 128/203.15; 128/206.11; 128/200.24

(58) Field of Classification Search ............. 128/200.11, 128/200.12, 200.13, 200.14, 200.16, 200.18, 128/200.23, 200.24, 203.12, 203.15, 203.16, 203.17, 203.18, 203.19, 203.21, 203.22, 204.12, 206.29, 207.13, 207.18; 239/330, 310, 322, 338, 350, 337, 586; 222/386, 378, 321.1, 321.6, 321.7, 321.8, 381, 391, 327, 326, 160, 162, 163; 604/151, 207, 211, 131, 209, 232, 208, 27, 28, 30, 36, 94.01; 606/199, 204.45
See application file for complete search history.

(56) References Cited

U.S. PATENT DOCUMENTS
2,078,180 A * 4/1937 Kronenberg .................... 604/28
(Continued)

FOREIGN PATENT DOCUMENTS
DE    32 38 149 A1    4/1984
(Continued)

OTHER PUBLICATIONS
H. Kauf, "Ability of Aerosols to Penetrate Paranasal Sinuses", Archiv klin. exper. Ohren-, Nasen-und Kehlkopfheilk., 190, pp. 95-108, 1968.
(Continued)

*Primary Examiner* — Justine R Yu
*Assistant Examiner* — Annette F Dixon
(74) *Attorney, Agent, or Firm* — Wolf, Greenfield & Sacks, P.C.

(57) ABSTRACT

A therapeutic aerosol device in which an aerosol generated by a nebulising device is supplied through a nosepiece to a patient's nostril so that the main aerosol flow supplied is able to emerge from the other nostril. The main aerosol flow is superimposed by pressure fluctuations. In order to guarantee that, due to the pressure fluctuation, aerosol is transported to the paranasal sinuses, a low resistance device is provided in the other nostril.

33 Claims, 6 Drawing Sheets

U.S. PATENT DOCUMENTS

| | | | |
|---|---|---|---|
| 2,582,529 A | | 1/1952 | Curry et al. |
| 4,029,095 A | * | 6/1977 | Pena .............................. 604/30 |
| 4,268,460 A | * | 5/1981 | Boiarski et al. ................... 261/1 |
| 4,273,124 A | * | 6/1981 | Zimmerman ............ 128/207.18 |
| 4,429,835 A | | 2/1984 | Brugger et al. |
| 4,951,661 A | * | 8/1990 | Sladek ..................... 128/202.27 |
| 5,054,477 A | * | 10/1991 | Terada et al. ............ 128/200.14 |
| 5,584,285 A | * | 12/1996 | Salter et al. .............. 128/200.21 |
| 5,687,715 A | * | 11/1997 | Landis et al. ............ 128/207.18 |
| 5,871,009 A | | 2/1999 | Rydgren |
| 5,890,491 A | * | 4/1999 | Rimkus .................... 128/206.11 |
| 5,928,190 A | * | 7/1999 | Davis ........................ 604/94.01 |
| 6,636,767 B1 | * | 10/2003 | Knudson et al. ................. 607/42 |
| 6,715,485 B1 | * | 4/2004 | Djupesland ............. 128/203.15 |
| 7,059,320 B2 | | 6/2006 | Feiner et al. |
| 7,225,807 B2 | * | 6/2007 | Papania et al. ........... 128/203.12 |
| 2007/0181133 A1 | | 8/2007 | Boehm et al. |

FOREIGN PATENT DOCUMENTS

| | | |
|---|---|---|
| DE | 36 17 400 A1 | 11/1987 |
| DE | 200 19 479 U1 | 3/2001 |
| EP | 0 507 707 B1 | 10/1992 |
| EP | 0 652 021 A1 | 5/1995 |
| EP | 0 732 111 A2 | 9/1996 |
| EP | 1 180 378 A2 | 2/2002 |
| FR | 1 567 403 | 5/1969 |
| FR | 2 639 236 A1 | 5/1990 |
| WO | WO 00/51672 A1 | 9/2000 |
| WO | WO 01/02024 A1 | 1/2001 |
| WO | WO 01/34232 A1 | 5/2001 |
| WO | WO 03/082393 A1 | 10/2003 |
| WO | WO 2004/004814 A2 | 1/2004 |
| WO | WO 2004/020029 A1 | 3/2004 |

OTHER PUBLICATIONS

Hyo et al., Particle deposition efficiency of therapeutic aerosols in the human maxillary sinus, Rhinology, 27, pp. 17-26, 1989.

Search report mailed Dec. 12, 2003 from corresponding International Application No. PCT/EP03/09862.

Search Report mailed Jul. 6, 2007 from European Application No. 07007418.2.

Extended Search Report issued on Jun. 3, 2008 from European Application No. 1 806 157.

\* cited by examiner

THERAPEUTIC AEROSOL DEVICE

FIELD OF THE INVENTION

The invention relates to a therapeutic aerosol device in which an aerosol generated in a nebulising device is supplied through a nosepiece to a patient's naval cavities in the form of a main aerosol flow.

BACKGROUND OF THE INVENTION

Known in this context from "Ability of Aerosols to Penetrate Paranasal Sinuses" H. Kauff. Archive. klin. Exper. Ohren-,Nasen- and Kehlkopfheilk. 190, 95-108 (1968) is that pressure fluctuations and vibrations can cause aerosols to penetrate the paranasal sinuses through which the main aerosol flow through the nasal cavities does not actively flow. An example of the application of these findings is known from EP 0 507 707 A1. According to this, an aerosol flow is superimposed with pressure fluctuations which are intended to cause the aerosol particles/droplets in the main aerosol flow to pass through the ostia and enter the paranasal sinuses.

In this way, although the main aerosol flow does not directly flow through the paranasal sinuses, they can be reached and treated by a drug administered in aerosol form. As with other types of aerosol therapy, it is attempted to deposit sufficient quantities of the drug at the desired points, for which in the case of the paranasal sinuses a sufficient quantity of the aerosol in the main aerosol flow must pass through the ostia and penetrate the paranasal sinuses.

Experimental investigations on different models of human nose have demonstrated that when known therapeutic aerosol devices are used deposition in the paranasal sinuses is less than expected and desired. The opening size of the ostia, which due to the disease is often extremely small, also has a greater influence on deposition than generally assumed.

SUMMARY OF THE INVENTION

Against this background, the object of the invention is to disclose suitable measures for increasing the deposition of an aerosol in the paranasal sinuses to enable therapeutically useful and predictable deposition in the paranasal sinuses through which there is no active flow.

This object is achieved by a therapeutic aerosol device with a) a nebuliser device including an aerosol generator to which a gaseous medium, in particular air and preferably compressed air for the generation of a main aerosol flow may be supplied from a supply device, preferably a compressed air supply device, and a pressure connection device to supply pressure fluctuations which are superimposed on the aerosol main flow, b) a nosepiece to supply the aerosol into one of the two alae of the nose of a user connected to the nebuliser device, and c) a flow resistance device at the other of the two alae of the user's nose.

The invention is based on the finding obtained in the experimental investigations that when an aerosol flow is supplied to a patient's nostril and then flows through the two nasal cavities, very surprisingly, one of the most decisive factors is the flow resistance presented to the pressure fluctuations at the other nostril. Only when there is flow resistance at the other nostril do the superimposed pressure fluctuations result in aerosol from the main aerosol flow through the nose reaching the paranasal sinuses as well and the aerosol being deposited there.

BRIEF DESCRIPTION OF THE DRAWINGS

The invention will be further described with reference to examples of embodiments in the drawings. The drawings show.

DETAILED DESCRIPTION

Figure 1:
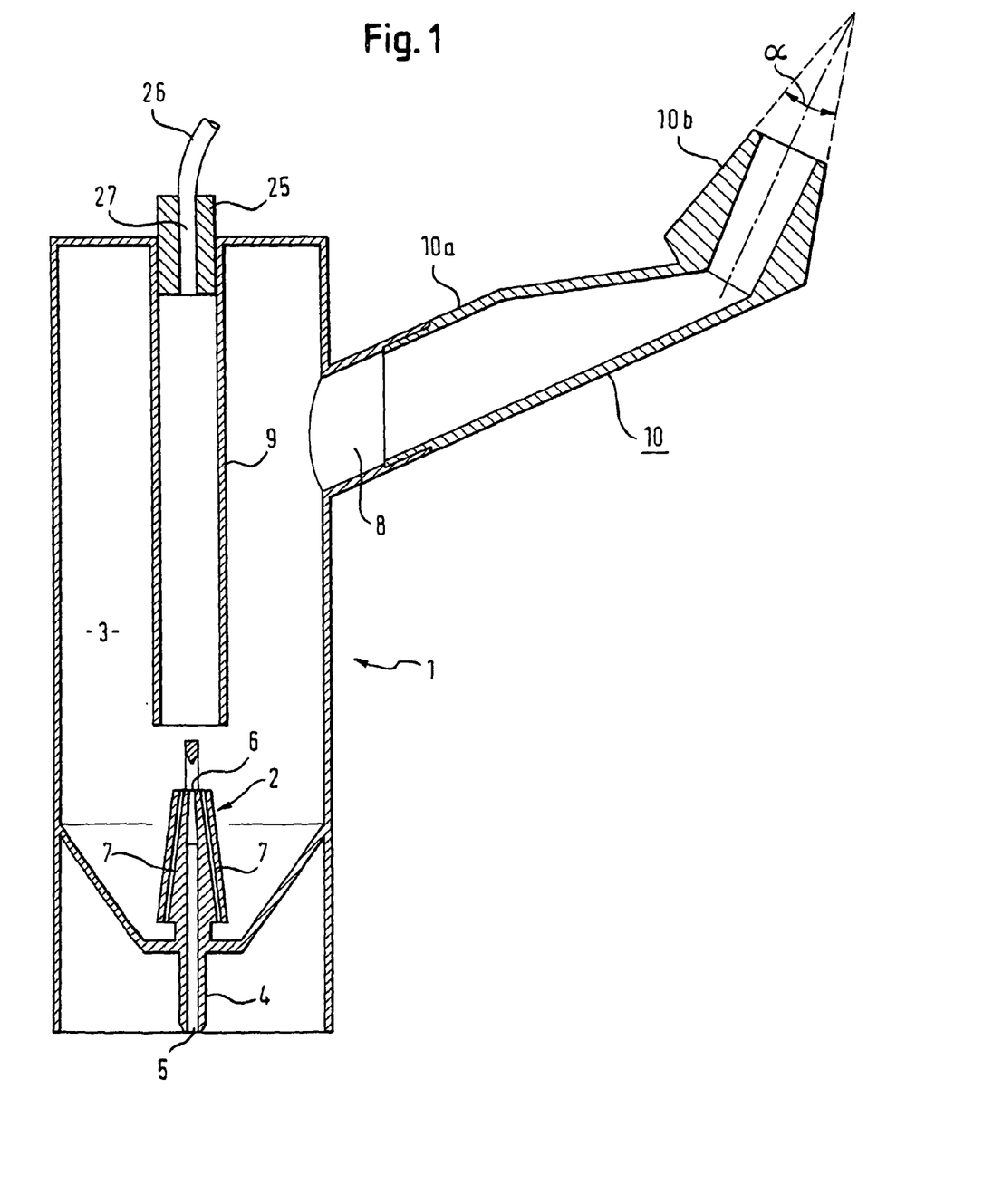
FIG. 1 a view of a therapeutic aerosol device according to the invention

FIG. 1 shows a nebulising device 1 comprising an aerosol generator 2 arranged in a nebulising chamber 3. A liquid supplied at the foot of the aerosol generator is nebulised by means of the aerosol generator 2 when compressed air is supplied to the aerosol generator 2 via a connector 4 arranged at one end (at the bottom of FIG. 1) of the aerosol generator. The compressed air flows through a compressed air channel 5 arranged centrally in the aerosol generator and emerges at the other end of the aerosol generator from a nozzle opening 6. The liquid is drawn in through the suction channels 7, which are arranged next to the nozzle opening and extend in the aerosol generator from the level of the nozzle opening to the foot of the aerosol generator and open towards the liquid supplied there, and nebulised into the nebulising chamber 3 in the area in front of the nozzle opening 6.

In the case of aerosol therapies directed at the upper respiratory tracts, the bronchial tract and the lungs, a patient inhales the aerosol generated in this way whereby he withdraws the aerosol on inhaling through a mouthpiece attached to a connecting piece 8 on the nebulising device. Hereby, ambient air flows through an air inlet flue 9 as required into the nebulising chamber 3 when the aerosol is withdrawn from the nebulising chamber 3 during the inhalation phase.

In the case of aerosol therapies directed at the nasal cavity, the mouthpiece is replaced by a nosepiece 10 arranged at one end 10a for attachment to the connecting piece 8 on the nebulising device 1 while the other end 10b is designed so that it may be introduced in a nostril in a patient's nose and seal it tightly. The end 10b preferably takes the shape of a truncated cone with an aperture angle α in a range of from 10° to 40°. Hereby, the longitudinal axis of the truncated cone is inclined in relation to the longitudinal axis of the connecting piece 8 so that, when the nebuliser is held vertically, the nosepiece may be placed simply and comfortably in the patient's nostril.

In this way, the aerosol generated in the nebuliser device is supplied to one nostril and hence one nasal cavity of the patient. The compressed air supplied to the nebuliser device for the generation of the aerosol, ensures that there is a sufficient aerosol main flow in or through the patient's nose. The main aerosol flow runs from one nostril through one nasal cavity to the other nasal cavity. This main aerosol flow is superimposed by pressure fluctuations as described in more detail below. Without further measures, the main aerosol flow emerges from the other nostril in the patient's nose when the patient, as is usual with aerosol therapies for the paranasal sinuses, seals the nasal cavities from the throat and mouth by means of the soft palate.

According to the invention, as an additional measure a flow resistance device 11 is arranged in the patient's other nostril (FIGS. 2 to 5) by means of which a flow resistance for the pressure fluctuations and the main aerosol flow is established which is higher than the resistance of the natural flow path through the patient's nose. It is only with the significantly higher flow resistance at the other nostril and hence at the other end of the flow path of the main aerosol flow through the patient's nose that an effective quantity of the aerosol is able to penetrate the paranasal sinuses.

Figure 2:
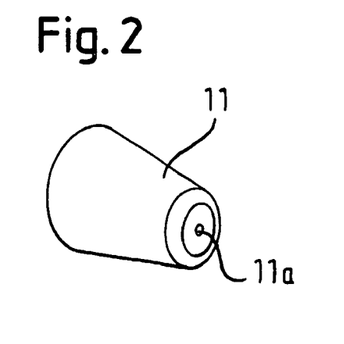
FIG. 2 a view of a flow resistance device according to the invention
Figure 3:
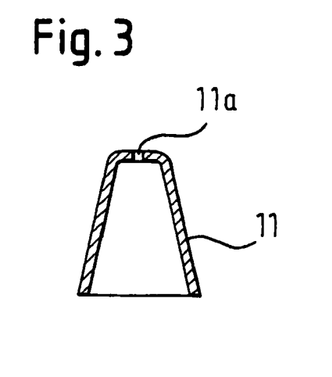
FIG. 3 another view of a flow resistance device according to the invention
Figure 4:
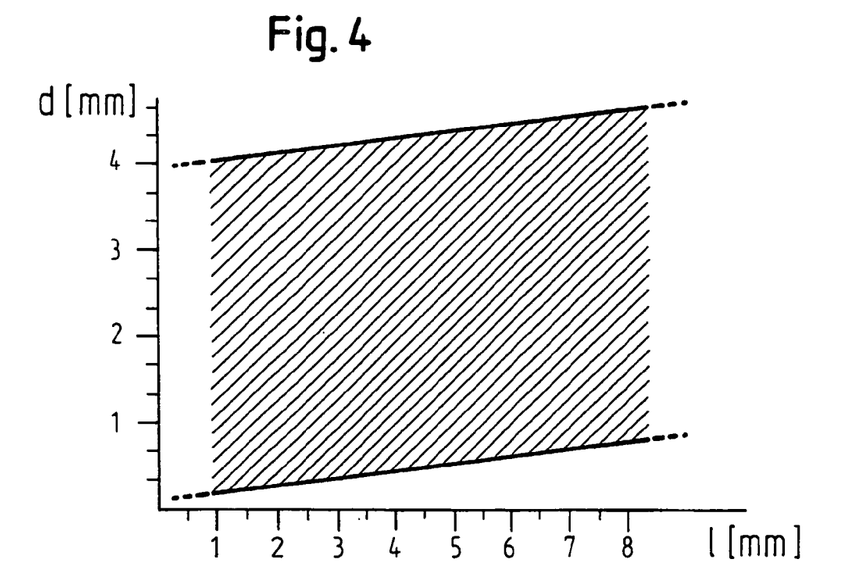
FIG. 4 a diagram for the determination of effective diameter/length value pairs for a flow resistance device according to the invention FIG. 5A a cross-sectional view of another flow resistance device according to the invention FIG. 5B a cross-sectional view of another flow resistance device according to the invention FIG. 6 another view of a flow resistance device according to the invention FIG. 7 a view of a device for the generation of pressure fluctuations FIG. 8 a view of a flow resistance device according to the invention with an alternatively embodied connection device FIG. 9 an alternative therapeutic aerosol device according to the invention FIG. 10 an alternative nosepiece for a therapeutic aerosol device according to the invention FIG. 11 a first example of an embodiment of a sensor device on an flow resistance device according to the invention, and FIG. 12 a second example of an embodiment of a sensor device on a flow resistance device according to the invention

The flow resistance at the patient's other nostril may be realised, for example, in the form of a stopper 11 with a small opening 11a as shown in FIGS. 2 and 3. The stopper has a basically conical shape with an aperture angle α in a range from 10° to 40° adapted to the nostrils in a human nose and which hence ensures a secure fit. The stopper is preferably hollow as may be seen in FIG. 3 and comprises at the tapered end a drill-hole 11a through which the main aerosol flow emerges from the patient's nose. The diameter d of the drill-hole and its length l determine the flow resistance against the main aerosol flow. As the representation in FIG. 2 or 3 shows, the flow resistance according to the invention is evidently greater than the flow resistance of the natural flow path through the patient's nose without the flow resistance device 11. FIG. 4 shows as an example a range of possible value pairs of diameter d and length l for opening 11a in a flow resistance device according to the invention. Suitable values for d and l may be determined from this range, which is shown with a grey background in FIG. 4.

Figure 5A:
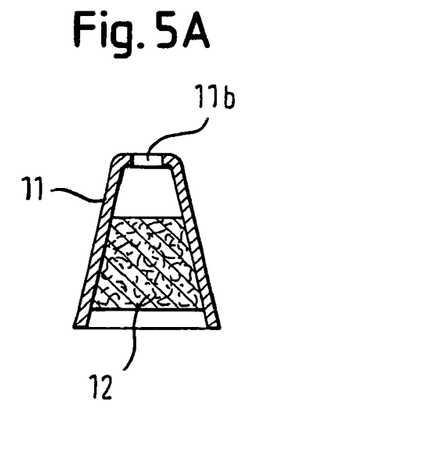

In an alternative embodiment as shown in FIG. 5A the hollow space in the stopper 11 is filled at least partially with a filter material 12 which, due to its filter properties, has increased flow resistance. In one embodiment, the drill-hole 11b may be embodied larger, as FIG. 5 shows since the increase in the flow resistance is also due to the filter material 12. The filter material 12 also ensures that aerosol remnants are filtered off before they are able to escape into the environment. With some drugs, the escape of even the minutest quantities is undesirable so that any measure to reduce the amount released is welcome.

Figure 5B:
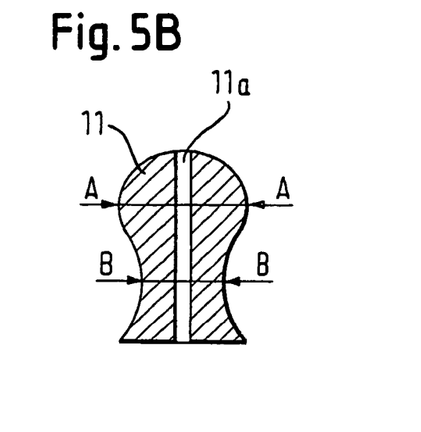

FIG. 5B shows a further embodiment of a flow resistance device according to the invention in the form of a stopper 11 comprising a first area A-A with a large diameter and a second area B-B with a small diameter. The areas merge into each other so that overall a bell shape is produced which is penetrated by opening 11a in the longitudinal direction. Area A-A is introduced into the nostril and ensures a reliable and tight fit of the flow resistance device 11 according to the invention as is also the case with the other embodiments. A hollow space may also be provided in the interior of the embodiment according to FIG. 5B, as described and demonstrated with reference to FIG. 3. A filter may also be arranged in the hollow space as shown in FIG. 5A.

Figure 6:
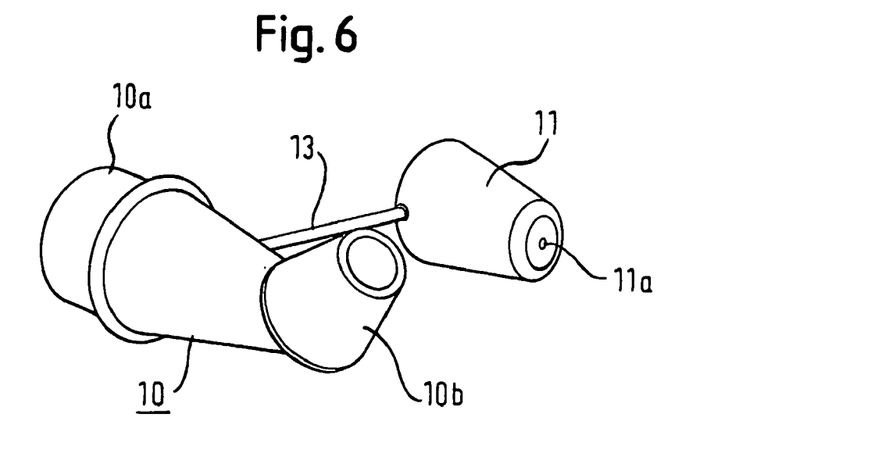

In order to simplify the handling of the nosepiece and in particular to prevent the stopper being lost, the stopper is preferably connected to the nosepiece, as shown in FIG. 6. This may be achieved by means of a flexible connecting element 13 which suggests the one-piece embodiment of the nosepiece 10 and the flow resistance device 11 from one and the same material. The flow resistance device 11 may alternatively be equipped with a ring arranged on the remote end of the connecting element 13 and which may be plugged onto the nosepiece 10 to secure the stopper on the nosepiece.

It also seems opportune to combine several flow resistance devices 11 each with a different flow resistance to form one therapeutic set and give the patient the option of changing the flow resistance devices 11 during aerosol therapy. This takes into account the changing conditions in the patient's nasal cavities during the course of the therapy and achieves a further improvement. For example, starting with a high flow resistance it is possible to change gradually to a lower flow resistance in order to adapt the therapy as the ostia expand in response to the therapy. It is also possible and advisable to adapt the flow resistance according to the type or method of administration of the drug in particular with regard to the embodiment with a filter.

Figure 7:
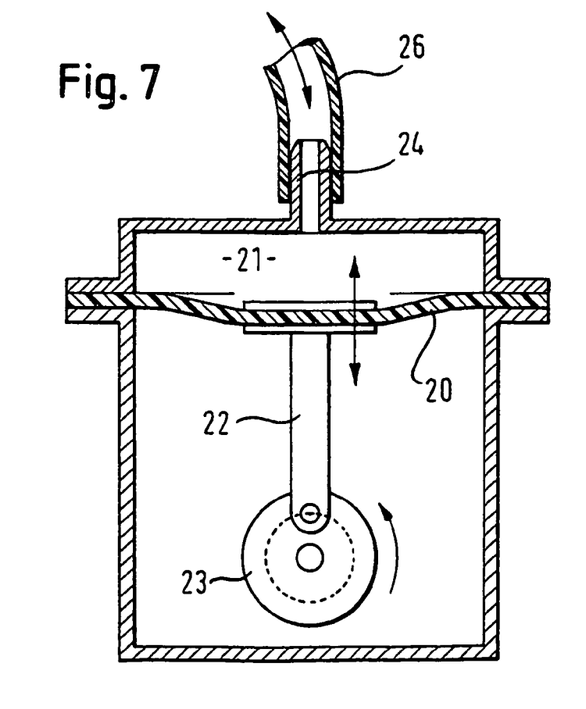

The pressure fluctuations characterising the main aerosol flow may be generated in different ways. As shown in FIG. 7, the pressure fluctuations may be generated by a membrane 20, which seals a hollow space 21 (pressure chamber) in a pressure-tight way, if the membrane 20 is moved to and fro by a piston rod 22. For this, the piston rod 22 is supported eccentrically on a driving pulley 23 so that the piston rod 22 causes a pressure-fluctuation-generating movement of the membrane 20 when the driving pulley 23 turns. For this, the driving pulley 23 is connected to an electric motor (not shown) or another suitable drive.

The movement of the membrane 20 exposes the air column, which is in the pressure chamber 21 and in a hose line 26 connected to a connection piece 24 on the pressure chamber 21, to pressure fluctuations which are sent to the nebuliser device 1 to be superimposed on the main aerosol flow. For this, according to the invention a pressure connection device 25, shown in FIG. 1, is provided on the nebuliser device 1. Hereby, a particularly advantageous further embodiment of the invention for the achievement of the object mentioned at the beginning has been found to be the provision of a connection on the air inlet flue 9 in the nebulising device 1, as shown in FIG. 1. This method of imposing the pressure fluctuations on the main aerosol flow is characterised by a high deposition of aerosol in the paranasal sinuses. Particularly good deposition values may be obtained in particular with this type of connection to the nebuliser, but also with other embodiments of the connection, if the frequency of the pressure fluctuations lies within a range of from 10 to 100 Hz, preferably in the range from 15 to 55 Hz.

Figure 8:
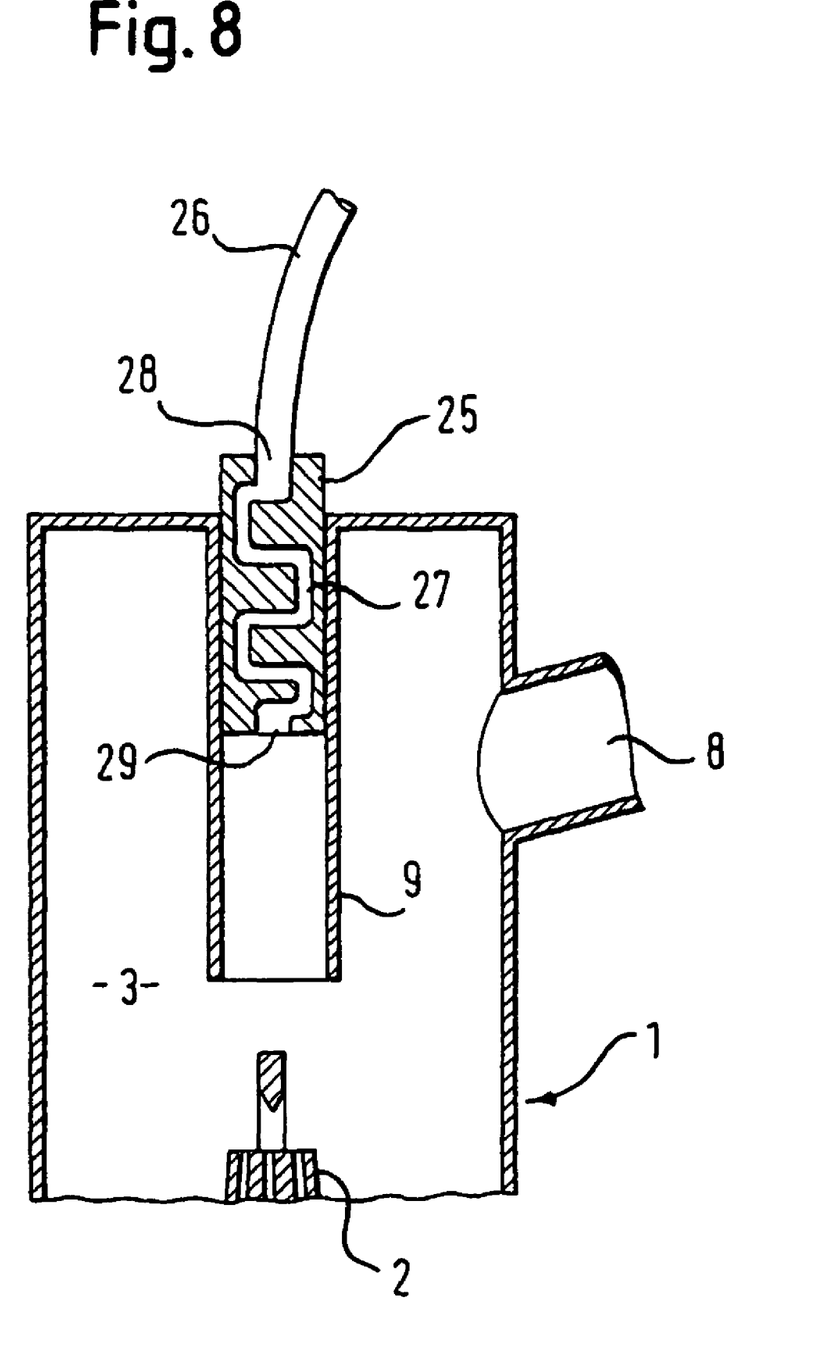

FIG. 8 shows an example of an embodiment of the connection device 25 for the hose line 26 arranged on the inlet air flue 9 in the nebulising device 1. The connection device 25 according to FIG. 8 is embodied as an aerosol trap and also comprises by way of example a meander-shaped embodiment of the connecting section 27 which runs from the connection point 28 in the hose 26 to the outlet aperture 29 in the interior of the air inlet flue 9. The meander-shaped design means that the pressure fluctuations sent via the hose line 26 to the nebuliser device 1 in order to be superimposed on the main aerosol flow do not convey the aerosol into the hose line 26. The meandering route of the connecting area 27 ensures that aerosol conveyed in this area is precipitated and accumulated on the walls of the connecting section 27 in order preferably by means of a suitable design, for example an inclined design, of the connecting area 27 to be then returned to the interior of the nebuliser 1.

Figure 9:
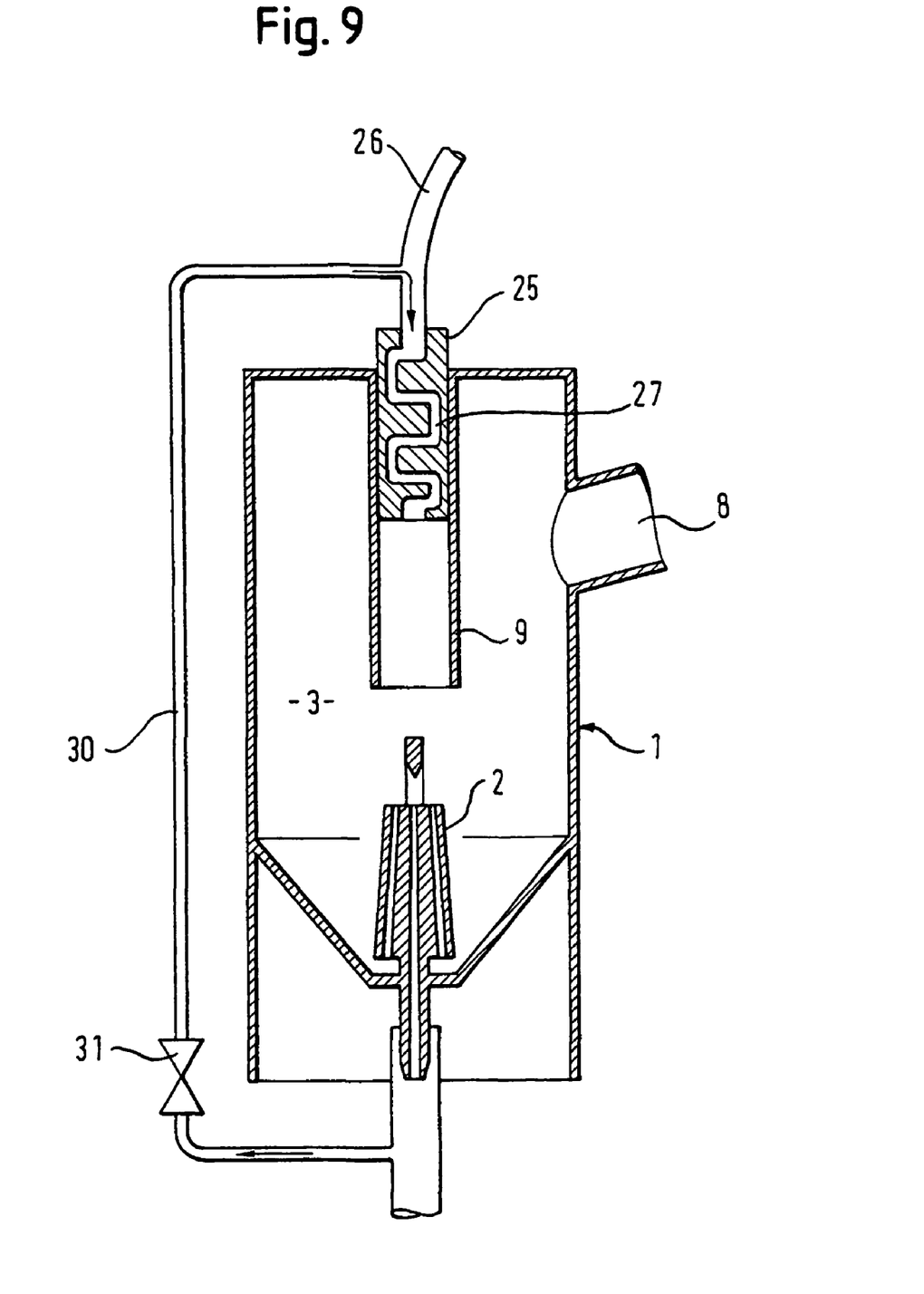

FIG. 9 shows a further embodiment of the device according to the invention in which part of the compressed air supplied to the aerosol generator 2 is tapped off in order to be supplied via the connecting device 25 for the hose line 26 into the nebuliser device 1. This ensures that, in addition to the pressure fluctuations via the inlet air flue 9, a flow of air is directed into the nebuliser device 1 to prevent aerosol being conveyed into the hose line 26. Provided in the line 30 conveying the partial flow to the connecting device is a throttle 31 that reduces the pressure of the partial flow. FIG. 9 shows that the partial flow is provided in addition to the meander-shaped design of the connecting section 27 in the connecting device 25. However, alternatively the partial flow may also be used together with the connecting device 25 shown in FIG. 1 in order to prevent the aerosol from being transported into the hose line 26.

Figure 10:
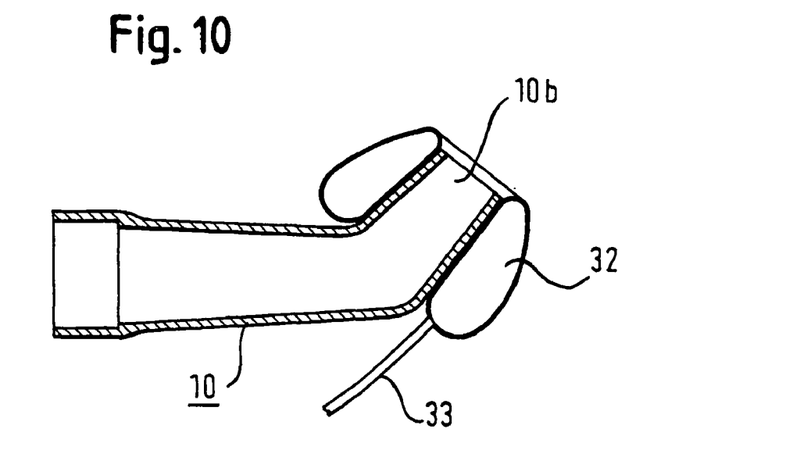

FIG. 10 shows another embodiment of the nosepiece 10 according to the invention. In this example of an embodiment, the end 10*b* which is designed for the introduction of the nosepiece 10 into a patient's nostril comprises an inflatable balloon device 32 which may be operated via a compressed air supply line 33, for example with the compressed air supply for the aerosol generator 2, preferably via a throttle or with a manually operated pump. The balloon device 32 encloses the end 10*b* of the nosepiece 10 in an annular shape whereby the balloon device 32 has a cross section emulating a truncating cone when the balloon device 32 is inflated. When the nosepiece 10 has been introduced into the patient's nose, the balloon device 32 is filled with air and thereby expanded so that it lies tightly on the inner wall of the patient's nostril. This ensures that the nosepiece 10 sits securely and tightly in the patient's nostril. To remove the nosepiece 10, the pressure is relieved from the balloon device 32 again. A balloon device of this type is also possible on the flow resistance device according to the invention.

Figure 11:
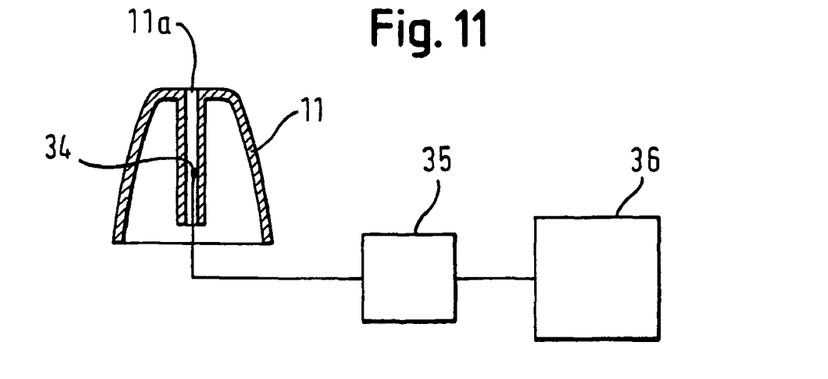

FIG. 11 shows a flow resistance device 11 according to the invention with an opening 11*a* in which a pressure sensor 34 is arranged in the drill-hole 11*a*. The pressure sensor 34 supplies an output signal to an evaluation device 35 that evaluates the signal and indicates to the patient on a display device 36 whether pressure fluctuations are identified to a sufficiently high degree or not. This supplies the patient with an acoustic or optical display enabling him to seal off the nasal cavity by means of the soft palate. The display device 36 may comprise light emitting diodes, for example in the colours red, yellow and green, in order to indicate a good, moderate or poor seal or other optical or acoustic display devices.

Figure 12:
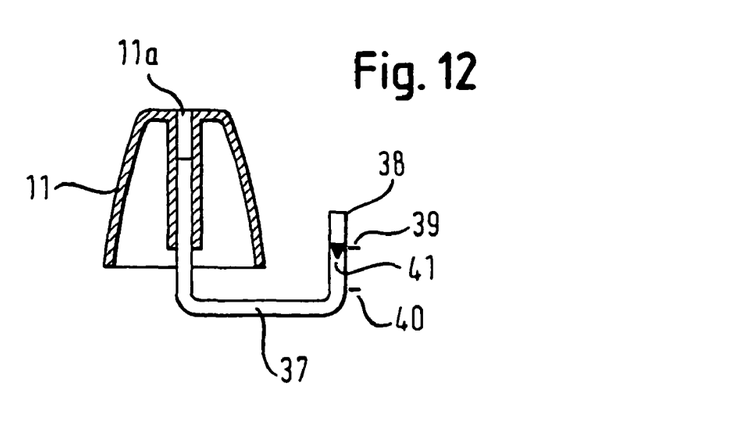

FIG. 12 shows a purely mechanical solution which consists in the fact that connected to the drill hole 11*a* of a flow resistance device 11 is a transparent display line 37 which has two markings 39 and 40 at an end 38 visible to the patient. A display element 41 is provided in the display line 37 and moves under the influence of the main aerosol flow which flows through the flow resistance device 11. If the nasal cavity is closed by the patient's soft palate, the main aerosol flow passes through the drill-hole 11*a* in the flow resistance device 11 and moves the display element 41 in the area of the marking 39 so that the patient can see that the nasal cavity has been effectively sealed. If it is not sealed, the display device 41 drops to marking 40 thus signalling to the patient that a therapeutic fit has not been achieved.

The purpose and object of the aerosol device according to the invention is the targeted introduction of active ingredients into the hollow cavities in the area of the nose and frontal sinus. Due to anatomical reasons, these areas are poorly supplied with blood and frequently poorly ventilated and therefore active ingredients administered orally or parenterally do not reach the site of action in therapeutically efficacious concentrations. Since the access points are very small and frequently obstructed, preferably only the only drug formulations supplied to the site should be those that may be transported with aerosol droplets and have diameters of less than 10 μm and preferably approximately 2 to 5 μm. The therapeutic action may be improved by the use of surface-active and adhesive excipients in the active ingredient formulations because such excipients improve spreadability and wettability. Recommended to reduce the swelling of the mucous membrane is the application of vasoconstrictive substances before or in combination with anti-inflammatory and anti-allergenic active ingredients, for example corticoids and/or antibiotics.

It is noted that the inventive therapeutic aerosol device may be at least partially integrated into a handheld device, such as a hand held aerosol device having a manually operated supply device for generating an aerosol flow, such as a manually operated pump.

The following classes of active ingredients or substances can be applied by means of the device according to the invention:

Substances with an anti-inflammatory action, for example: betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone aceponate, hydrocortisone buteprate buteprate, hydroxycortisone-17-butyrate, prednicarbate, 6-methylprednisolone aceponate, mometasone furoate, elastane, prostaglandin, leukotriene, bradykinin antagonists, non-steroidal anti-inflammatory drugs (NSAIDs) and/or anti-infective agents, for example: antibiotics with or without beta-lactamase inhibitors, for example clavunalic acid, sulbactam, tazobactam, etc. from the class of penicillins, for example: benzylpenicillins (penicillin-G-sodium, clemizone penicillin, benzathine penicillin G); phenoxypenicillins (penicillin V, propicillin); aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), amiidine penicillin (mecillinam) cefalosporins, for example: cefazolins (cefazolin, cefazedone); cefuroximes (cerufoxim, cefamdole, cefotiam); cefoxitins (cefoxitin, cefotetan, latamoxef, flomoxef); cefotaximes (cefotaxime, ceftriaxone, ceftizoxime, cefmenoxime); ceftazidimes (ceftadzidime, cefpirome, cefepime); cefalexins (cefalexin, cefaclor, cefadroxil, cefradine, loracarbef, cefprozil); cefiximes (cefixime, cefpodoxim proxetile, cefuroxime axetil, cefetamet pivoxil, cefotiam hexetil)

cabapenems and combinations, for example imipenem±cilastin, meropenem, biapenem and monobactams (aztreonam), the above antibiotics, and/or aminoglycosides, for example: gentamicin, amikacin, isepamicin, arbekacin, tobramycin, netilmicin, spectinomycin, neomycin, paromoycin, kanamycin, and/or macrolides, for example: erythromycin, clarythromycin, roxithromycin, azithromycin, dithromycin, josamycin, spiramycin, and/or gyrase inhibitors, for example: ciprofloxacin, gatifloxacin, norfloxacin, ofloxacin, levofloxacin, perfloxacin, lomefloxacin, fleroxacin, clinafloxacin, sitafloxacin, gemifloxacin, balofloxacin, trovafloxacin, moxifloxacin, and/or antibiotics of other classes of active ingredients, for example: tetracyclines (doxycycline, minocycline), glycopeptides (vancomycin, teicoplanin, peptide 4), polymyxins (polymyxin B, colistin), tithromycin, lincomycin, clindamycin, oxazolindiones (linzezolids), chloramphenicol, fosfomycin, rifampicin, isoniazid, cycloserine, terizidone, ansamycin pentamidine, and/or sulfonamides and combinations, for example: sulfadiazine, sulfamethoxazole, sulfalene, co-trimoxazole, co-trimetrol, co-trimoxazine, co-tetraxazine, and/or nitroimidazoles and nitrofurans, for example, metronidazole, tinidazole, ornidazole, nitrofurantoin, nitrofuranzone, and/or antimycotics, for example: azole derivatives (clotrimazole, oxiconazole, miconazole, ketoconazole, itraconazole, fluconazole); polyene antibiotics (amphotericin B, natamycin, nystatin, flucocytosine), and/or virustatics, for example: podophyllotoxin, vidarabine, tromantadine, zidovudine, proteinase inhibitors, alone or also in combination with:

extracts or ingredients of plants, for example: camomile, hamamelis, echiancea and calendula extract, essential oils (eucalyptus oil, camomile oil, pine needle oil, spruce needle oil, peppermint oil, thyme oil, rosemary oil), bisabol, cineole, myrtol, thymol, menthol, camphor and/or wound treatment agents and anti-oxidants, for example: dexpanthenol, iodine povidone, tannin, bismuth salts, allantoin, zinc compounds, vitamins and trace elements, cod liver oil extract, tocopherols, glutathione, ascorbic acid, and/or antiseptics: acridine derivatives, benzoates, rivanol, chlorhexetidine, quarternary ammonium compounds, cetrimides, biphenylol, clorofene, octenidine, and/or mucolytics, for example: acetylcysteine, carbocysteine, ambroxol, bromhexine, tyloxapol, recombined surfactant proteins, DNase, and/or substances to reduce swelling of the mucous membrane, for example: phenylephrine, naphazoline, tramazoline, tetryzoline, oxymetazoline, fenoxazoline, xylometazoline, epinephrine, isoprenaline, hexoprenaline, ephedrine, antiallergic agents (DSCG), heparin, heparinoids, and/or local anaesthetics, for example: tetracaine, procaine, lidocaine.

The aforementioned substances are preferably used in the form of their usual pharmaceutical configurations or as salts, esters, isomers, stereoisomers, diastereomers, epimers, etc. with the objective in each case of obtaining a pharmaceutical form that it stable when stored. For this, formulations may be used in a wide variety of pharmaceutical forms, for example as solutions, suspensions, emulsions, powders or lyophilisates etc. in 2 chamber systems with aqueous or non-aqueous solvents or mixtures, etc. It is advantageous to use excipients that improve solubility for example glycerol, propylene glycol, ethanol, encourage penetration of the paranasal sinuses and frontal sinuses, reduce surface tension and/or prolong the deposition time and dwell time (control release) at the site in question, which may be achieved, for example, by the addition of non-ionic surfactants, for example tyloxapol, vitamin E-TPGS, polysorbates, pluronics, etc. and/or other additives for example phospholipids, cellulose ether, dextrans, chitosans, cyclodextrines, polyvinylpyrrolidone, polyvinyl alcohol, etc.

Also claimed as inventive is the formulation and application of the aforementioned classes of active ingredients and substances as liposomes, suspensions and emulsions in the micrometer range and preferably in the nanometer ranger with a geometric diameter of less than approximately 1 µm that are particularly suitable for transportation by small droplets. This ensures that by means of the device according to the invention these preparations are better able to penetrate the paranasal sinuses and frontal sinuses and be deposited and hence develop their action. Active ingredients that have to be used as solid formulations due to their poor storage stability in solution may be either dissolved or suspended with a suitable aqueous or non-aqueous solvent (for example glycerol, propylene glycol, polyglycols, pluronics, ethanol) or mixtures thereof shortly before application. Also claimed is a coating and encasing method to make malodorous or locally irritant substances more tolerable for application by complexation, for example with cyclodextrins. Alternatively, these active ingredients may also be bonded to polymeric excipients, for example chitosan and cellulose ether derivatives or gelatins in order to modify the absorption properties in such a way that the therapeutic effect may be intensified and the application frequency reduced. It is advantageous to use isotonic or hypertonic solutions containing soluble alkali and alkaline-earth salts (for example Emser salts, magnesium chloride, sodium hydrogen carbonate, etc.) and have a physiological pH range of 4-9.

This may be achieved by the addition of common pharmaceutical buffer substances to the active ingredient formulations. The formulations may also be provided with pharmaceutically common aroma and taste correcting agents to improve their acceptance particular as far as children are concerned.

The invention claimed is:

1. Therapeutic aerosol device consisting of:
a) a nebuliser device including
aa) an aerosol generator to which a gaseous medium for the generation of a main aerosol flow may be supplied from a supply device, and
bb) a pressure connection device to supply pressure fluctuations which are superimposed on the aerosol main flow,
b) a nosepiece configured to supply the aerosol into one of the two alae of the nose of a user connected to the nebuliser device, and
c) a flow resistance device configured to be placed at the other of the two alae of the user's nose, the flow resistance device causing aerosol from the main aerosol flow having pressure fluctuations superimposed thereon to reach the paranasal sinuses of the user and to be deposited therein, the flow resistance device being interchangeable with other flow resistance devices having different flow resistances.

2. Therapeutic aerosol device according to claim 1, wherein the supply device is a compressed air supply device and the aerosol generator is a nebuliser nozzle with a compressed air channel opening into a nozzle opening, and with at least one suction channel through which a liquid to be nebulised is drawn in.

3. Therapeutic aerosol device according to claim 1, wherein the nosepiece is configured at one end for attachment to a connecting piece in the nebuliser device and at the other end is configured for introduction into one nostril and the tight sealing of one of a user's nostrils.

4. Therapeutic aerosol device according to claim 3, wherein the other end of the nosepiece is configured in the form of a truncated cone.

5. Therapeutic aerosol device according to claim 4, wherein the truncated cone shaped end of the nosepiece has a longitudinal axis, which is inclined relative to the longitudinal axis of the connecting piece of the nebuliser device.

6. Therapeutic aerosol device according to claim 5, wherein the angle between the longitudinal axes of the truncated cone shaped end and of the connecting piece is in the range of from 30° to 75°.

7. Therapeutic aerosol device according to claim 4, wherein the truncated cone has an aperture angle α in a range of from 10° to 40°.

8. Therapeutic aerosol device according to claim 3, wherein the other end of the nosepiece is configured with a balloon device that may be inflated by the supply of compressed air in order to ensure a reliable and tight fit of the nosepiece in one of a patient's nostrils.

9. Therapeutic aerosol device according to claim 1, wherein the flow resistance device is configured to have an opening smaller than the user's nostril.

10. Therapeutic aerosol device according to claim 1, wherein the flow resistance device comprises a filter device.

11. Therapeutic aerosol device according to claim 1, wherein the flow resistance device is connected to the nosepiece by a connecting element.

12. Therapeutic aerosol device according to claim 11, wherein the flow resistance device is embodied in one piece with the nosepiece.

13. Therapeutic aerosol device according to claim 1, wherein the flow resistance device is a stopper in particular a stopper with a hollow space.

14. Therapeutic aerosol device according to claim 13, wherein the stopper is embodied in the form of a truncated cone.

15. Therapeutic aerosol device according to claim 14, wherein the truncated cone has an aperture angle α in a range of from 10° to 40°.

16. Therapeutic aerosol device according to claim 13, wherein the stopper is embodied in a bell shape with a first area with a large diameter and a second diameter with a small diameter.

17. Therapeutic aerosol device according to claim 1, wherein the nebuliser device comprises an air inlet flue and the pressure connection device is intended to supply pressure fluctuations at the air inlet flue.

18. Therapeutic aerosol device according to claim 17, wherein the pressure connection device comprises a meander-shaped guide for the compressed air.

19. Therapeutic aerosol device according to claim 1, wherein compressed air is supplied through the pressure connection device.

20. Therapeutic aerosol device according to claim 1, wherein the frequency of the pressure fluctuations lies within the range from 10 to 100 Hz.

21. Therapeutic aerosol device according to claim 20, wherein the frequency of the pressure fluctuations lies within the range from 15 to 55 Hz.

22. Therapeutic aerosol device according to claim 1, wherein the pressure fluctuations are generated by means of a membrane compressor comprising a membrane that seals a pressure chamber in a pressure-tight way and is moved to and fro by a piston rod.

23. Therapeutic aerosol device according to claim 20, wherein the pressure chamber comprises a connecting piece for the connection of a hose line which is connected to the pressure connection device in the nebuliser device.

24. Therapeutic aerosol device according to claim 1, wherein a sensor device to determine the main aerosol flow or the pressure fluctuations is provided on the flow resistance device.

25. Therapeutic aerosol device according to claim 24, wherein an evaluation device and a display device are connected to the sensor device to indicate to the patient whether the main aerosol flow or the pressure fluctuations are sufficiently within the area of the flow resistance device.

26. Therapeutic aerosol device according to claim 24, wherein the sensor device comprises a movable display element which is arranged in a display section of the sensor device and is moved by the main aerosol flow or the pressure fluctuations.

27. Therapeutic aerosol device according to claim 1 for the application of one or more substances selected from the group consisting of:
  substances with an anti-inflammatory action, including betamethasone, beclomethasone, budesonide, ciclesonide, dexamethasone, desoxymethasone, fluoconolone acetonide, flucinonide, flunisolide, fluticasone, icomethasone, rofleponide, triamcinolone acetonide, fluocortin butyl, hydrocortisone aceponate, hydrocortisone buteprate buteprate, hydroxycortisone-17-butyrate, prednicarbate, 6-methylprednisolone aceponate, mometasone furoate, elastane-, prostaglandin-, leukotriene-, bradykinin-antagonists, non-steroidal anti-inflammatory drugs (NSAIDs) and/or
  anti-infective agents, including antibiotics with or without beta-lactamase inhibitors, for example clavunalic acid, sulbactam, tazobactam, etc. from the class of
  penicillins, including benzylpenicillins (penicillin-G-sodium, clemizone penicillin, benzathine penicillin G); phenoxypenicillins (penicillin V, propicillin); aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), amiidine penicillin (mecillinam), cefalosporins, for example: cefazolins (cefazolin, cefazedone); cefuroximes (cerufoxim, cefamdole, cefotiam); cefoxitins (cefoxitin, cefotetan, latamoxef, flomoxef); cefotaximes (cefotaxime, ceftriaxone, ceftizoxime, cefmenoxime); ceftazidimes (ceftadzidime, cefpirome, cefepime); cefalexins (cefalexin, cefaclor, cefadroxil, cefradine, loracarbef, cefprozil); cefiximes (cefixime, cefpodoxim proxetile, cefuroxime axetil, cefetamet pivoxil, cefotiam hexetil), cabapenems and combinations, for example imipenem±cilastin, meropenem, biapenem monobactams (aztreonam), the above antibiotics and/or
  aminoglycosides, including gentamicin, amikacin, isepamicin, arbekacin, tobramycin, netilmicin, spectinomycin, neomycin, paromoycin, kanamycin, and/or
  macrolides, including erythromycin, clarythromycin, roxithromycin, azithromycin, dithromycin, josamycin, spiramycin, and/or
  gyrase inhibitors, including ciprofloxacin, gatifloxacin, norfloxacin, ofloxacin, levofloxacin, perfloxacin, lomefloxacin, fleroxacin, clinafloxacin, sitafloxacin, gemifloxacin, balofloxacin, trovafloxacin, moxifloxacin, and/or
  antibiotics of other classes, including tetracyclines (doxycycline, minocycline), glycopeptides (vancomycin, teicoplanin, peptide 4), polymyxins (polymyxin B, colistin), tithromycin, lincomycin, clindamycin, oxazolindiones (linzezolids), chloramphenicol, fosfomycin, rifampicin, isoniazid, cycloserine, terizidone, ansamycin pentamidine, and/or sulfonamides and combinations, including sulfadiazine, sulfamethoxazole, sulfalene, co-trimoxazole, co-trimetrol, co-trimoxazine, co-tetraxazine, and/or nitroimidazoles and nitrofurans, including metronidazole, tinidazole, ornidazole, nitrofurantoin, nitrofuranzone, and/or antimycotics, including azole derivatives (clotrimazole, oxiconazole, miconazole, ketoconazole, itraconazole, fluconazole); polyene antibiotics (amphotericin B, natamycin, nystatin, flucocytosine, and/or virustatics, including podophyllotoxin, vidarabine, tromantadine, zidovudine, proteinase inhibitors, alone or also in combination with:

extracts or ingredients of plants, including camomile, hamamelis, echiancea and calendula extract, essential oils (eucalyptus oil, camomile oil, pine needle oil, spruce needle oil, peppermint oil, thyme oil, rosemary oil), bisabol oil, cineole, myrtol, thymol, menthol, camphor and/or wound treatment agents and anti-oxidants, including dexpanthenol, iodine povidone, tannin, bismuth salts, allantoin, zinc compounds, vitamins and trace elements, cod liver oil extract, tocopherols, glutathione, ascorbic acid, and/or antiseptics: including acridine derivatives, benzoates, rivanol, chlorhexetidine, quarternary ammonium compounds, cetrimides, biphenylol, clorofene, octenidine, and/or mucolytics, including acetylcysteine, carbocysteine, ambroxol, bromhexine, tyloxapol, recombined surfactant proteins, DNase and/or substances to reduce swelling of the mucous membrane, including phenylephrine, naphazoline, tramazoline, tetryzoline, oxymetazoline, fenoxazoline, xylometazoline, epinephrine, isoprenaline, hexoprenaline, ephedrine, anti-allergic agents (DSCG), heparin, heparinoids, and/or local anaesthetics, including tetracaine, procaine, lidocaine.

28. Therapeutic aerosol device according to claim 27, wherein application by means of a therapeutic aerosol device in accordance with claim 1 takes place in such a way that aerosol droplets with a diameter of less than 10 μm are generated.

29. Therapeutic aerosol device according to claim 28, wherein aerosol droplets with a diameter of 2 to 5 μm are generated.

30. Therapeutic aerosol device according to claim 27, wherein at least one of the substances is used as a liposome, suspension or emulsion in the micrometer range with a geometric diameter of less than 1 μm.

31. Therapeutic aerosol device according to claim 1, integrated into a handheld device.

32. Therapeutic aerosol device according to claim 1, wherein the supply device comprises an air supply device which supplies air.

33. Therapeutic aerosol device according to claim 1, wherein the supply device comprises a compressed air supply device which supplies compressed air.

* * * * *

UNITED STATES PATENT AND TRADEMARK OFFICE
CERTIFICATE OF CORRECTION

| | | |
|---|---|---|
| PATENT NO. | : 7,980,247 B2 | Page 1 of 1 |
| APPLICATION NO. | : 10/519011 | |
| DATED | : July 19, 2011 | |
| INVENTOR(S) | : Andreas Boehm et al. | |

It is certified that error appears in the above-identified patent and that said Letters Patent is hereby corrected as shown below:

At column 9, claim 23, line 66 should read as follows:

23. Therapeutic aerosol device according to claim 22,

Signed and Sealed this
Thirtieth Day of August, 2011

David J. Kappos
*Director of the United States Patent and Trademark Office*